United States Patent [19]

Devore

[11] Patent Number: 6,118,013

[45] Date of Patent: Sep. 12, 2000

[54] PREPARATION OF ADDITION POLYMERIZATION CATALYSTS

[75] Inventor: David D. Devore, Midland, Mich.

[73] Assignee: The Dow Chemical Company, Midland, Mich.

[21] Appl. No.: 09/302,067

[22] Filed: Apr. 29, 1999

Related U.S. Application Data

[63] Continuation of application No. 07/967,365, Oct. 28, 1992, abandoned, which is a continuation-in-part of application No. 07/702,475, May 20, 1991, abandoned.

[51] Int. Cl.$^7$ .............................. C07F 17/00; C07F 7/00
[52] U.S. Cl. .............................. 556/11; 534/15; 502/103; 502/117; 526/160; 526/943; 556/12; 556/21; 556/53; 987/2
[58] Field of Search .................. 556/11, 12, 21, 556/53; 534/15; 987/2; 502/103, 117; 6/160, 943

[56] References Cited

U.S. PATENT DOCUMENTS 5,455,333 10/1995 Stickler et al. ........................ 534/11

FOREIGN PATENT DOCUMENTS 0416815  3/1991  European Pat. Off. .

OTHER PUBLICATIONS

Szymoniak, Jan, et al., Inorganica Chimica Acta, 180 (1991) 153–160.

Reetz, Manfred T, Organotitanium Reagent in Organic Synthesis, Springer–Verlag, Berlin Heidelberg New York Tokyo, p. 181.

Pearson, Anthony J., Metallo–organic Chemistry, Wiley & Sons, pp. 114–116 (1985).

Collman, J. et al., Principles and Applications of Organotransition Metal Chemistry, University Science Books, 1987, 274–294; 307–309.

*Primary Examiner*—Porfirio Nazario-Gonzalez

[57] ABSTRACT

Metal complexes useful as components of addition polymerization catalysts are prepared by oxidizing Group 4 or Lanthanide metal containing complexes using an organic halide oxidizing agent in a unique one electron oxidation.

5 Claims, No Drawings

PREPARATION OF ADDITION POLYMERIZATION CATALYSTS

This is a continuation of application Ser. No. 07/967,365, filed Oct. 28, 1992, now abandoned, which is a continuation-in-part of application Ser. No. 07/702,475, filed May 20, 1991, now abandoned, the teachings of which are herein incorporated by reference in their entirety.

BACKGROUND OF THE INVENTION

The present invention relates to a process for forming addition polymerization catalysts. More particularly the present invention relates to such a process that utilizes low cost oxidizing agents to raise the oxidation state of transition metal cations in metal coordination complexes that are useful for addition polymerization catalysts by means of a one electron oxidation.

Numerous metal coordination complexes are known in the art. Especially useful are transition metal complexes including such complexes involving cyclopentadienyl and substituted cyclopentadienyl groups. Often such complexes are used in combination with an aluminum compound such as an aluminoxane to form catalytically active systems. Such complexes may be prepared by forming an initial complex wherein the metal cation is of a valence that is one less than that desired in the ultimate complex and oxidizing the metal to a higher valence using oxidizing agents such as silver or lead compounds. Disadvantageously however this procedure generates an undesirable heavy metal contaminated waste stream that must be disposed of. Thus it would be desirable if there were provided an oxidizing process for preparing transition metal complexes that does not generate heavy metal byproducts.

The present process is especially useful in preparing metal coordination complexes wherein the metal is bound to a delocalized substituted n-bonded moiety in a manner so as to induce a constrained geometry about the metal. Preferably the metal is bound to a cyclopentadienyl, substituted cyclopentadienyl or similar group by both a $\eta^5$-bond and a bridging linkage including other ligands of the metal. The complexes also preferably include metals having useful catalytic properties. Such complexes are disclosed and claimed in copending application Ser. No. 545,403, filed Jul. 3, 1990, the teachings of which are incorporated herein by reference thereto.

According to the present invention there is provided a process for preparing metal coordination complexes comprising a metal of Group 4 or the Lanthanide series of the Periodic Table of the Elements by means of oxidizing the metal of a selected complex to a higher oxidation state, characterized in that the oxidizing agent employed is an organic halide.

Preferred metal coordination complexes comprise a metal of Group 4 or the Lanthanide series of the Periodic Table of the Elements and a delocalized n-bonded moiety substituted with a constrain-inducing moiety, said complex having a constrained geometry about the metal atom such that the angle at the metal between the centroid of the delocalized, substituted n-bonded moiety and the center of at least one remaining substituent is less than such angle in a similar complex containing a similar n-bonded moiety lacking in such constrain-inducing substituent.

Preferred metal coordination complexes that may be prepared according to the present process correspond to the formula:

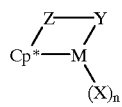

wherein:
M is a metal of Group 4, or the Lanthanide series of the Periodic Table of the Elements;
Cp* is a cyclopentadienyl or substituted cyclopentadienyl group bound in an $\eta^5$ bonding mode to M;
Z is a moiety comprising boron, or a member of Group 14 of the Periodic Table of the Elements, and optionally sulfur or oxygen, said moiety having up to 20 non-hydrogen atoms, and optionally Cp* and Z together form a fused ring system;
X independently each occurrence is an anionic ligand group having up to 30 non-hydrogen atoms, provided that in at least one occurrence X is halogen;
n is 1 or 2 depending on the valence of M; and
Y is an anionic ligand group bonded to Z and M comprising nitrogen, phosphorus, oxygen or sulfur and having up to 20 non-hydrogen atoms, and optionally Y and Z together form a fused ring system.

Thus the present process provides a process for preparing a metal coordination complex corresponding to the foregoing formula I comprising the steps of:

A) contacting a metal compound of the formula $MX_{n+1}$ or a coordinated adduct thereof with a dianionic salt compound corresponding to the formula:

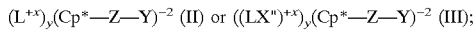

wherein:
X independently each occurrence is an anionic ligand group having up to 30 non-hydrogen atoms,
L is a metal of Group 1 or 2 of the Periodic Table of the Elements,
X" is the bromo, chloro or iodo,
x and y are either 1 or 2 and the product of x and y equals 2, and
M, Cp*, Z, and Y are as previously defined; in an inert solvent to form a complex corresponding to the formula:

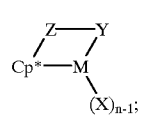

B) oxidizing the metal to a higher oxidation state by contacting the reaction product of step A) with an organic halide to raise the oxidation state of the metal and incorporate only the halogen ligand from the organic halide into the complex; and C) recovering the resulting product.

By use of the term "delocalized n-bonded moiety" is meant an unsaturated organic moiety, such as those comprising ethylenic or acetylenic functionality, wherein the n-electrons thereof are donated to the metal to form a bond. Examples include alkene-, alkenyl-, alkyne-, alkynyl-, allyl-, polyene-, and polyenyl-moieties as well as unsaturated cyclic systems.

By use of the term "constrained geometry" herein is meant that the metal atom is forced to greater exposure of the active metal site because of one or more substituents on the delocalized n-bonded moiety. Preferably the delocalized n-bonded moiety is a substituted cyclopentadienyl group having one or more substituents that form an extended structure which is ultimately covalently bonded to the metal atom. It is understood that each respective bond between the metal atom and the constituent atoms of the delocalized n-bonded moiety need not be equivalent. That is the metal may be symetrically or unsymetrically n-bound to the n-bonded moiety.

The geometry of the active metal site is further defined as follows. The centroid of the n-bonded moiety may be defined as the average of the respective X, Y, and Z coordinates of the atomic centers forming the n-bonded moiety. The angle, $\Theta$, formed at the metal center between the centroid of the n-bonded moiety and each other ligand of the metal complex may be easily calculated by standard techniques of single crystal X-ray diffraction. Each of these angles may increase or decrease depending on the molecular structure of the constrained geometry metal complex. Those complexes wherein one or more of the angles, $\Theta$, is less than in a similar, comparative complex differing only in the fact that the constrain-inducing substituent is replaced by hydrogen have constrained geometry for purposes of the present invention. Preferably one or more of the above angles, $\Theta$, decrease by at least 5% more preferably 7.5% compared to the comparative complex. Highly preferably, the average value of all bond angles, $\Theta$, is also less than in the comparative complex. Most preferably the metal coordination complex having constrained geometry is in the form of a ring structure, ie. the constrain-inducing substituent is part of a ring system which includes the metal.

Preferably, monocyclopentadienyl metal coordination complexes according to the present invention have constrained geometry such that the smallest angle, $\theta$, is less than 115°, more preferably less than 110°, most preferably less than 105°.

The term "activating cocatalyst" as used herein refers to a secondary component of the catalyst able to cause the metal-containing complex to become effective as an addition polymerization catalyst or alternatively to balance the ionic charge of a catalytically activated species. Examples of the foregoing activating cocatalysts for use herein include aluminum compounds containing an Al—O bond such as the alkylaluminoxanes, especially methylaluminoxane; aluminum alkyls; aluminum halides; aluminum alkylhalides; Lewis acids; ammonium salts; and mixtures of the foregoing.

Particular techniques for the preparation of aluminoxane type compounds are disclosed in U.S. Pat. No. 4,542,119 the teachings of which are incorporated herein in their entirety by reference thereto. In a particularly preferred embodiment an aluminum alkyl compound is contacted with a regeneratable water-containing substance such as hydrated alumina, silica, or other substance. A process for preparing aluminoxane employing such regeneratable substance is disclosed in copending application Ser. No. 91,566, filed Aug. 31, 1987 and assigned to the same assignee as the present patent application.

"Addition polymerizable monomers" include for example ethylenically unsaturated monomers, acetylenic compounds, conjugated or nonconjugated dienes, polyenes, carbon monoxide, etc. Preferred monomers include the $C_{2-10}$ α-olefins especially ethylene, propylene, isobutylene, 1-butene, 1-hexene, 4-methyl-1-pentene, and 1-octene. Other preferred monomers include styrene, halo- or alkyl substituted styrene, vinyl chloride, acrylonitrile, methylmethacrylate, tetrafluoroethylene, methacrylonitrile, vinylidene chloride, vinylbenzocyclobutane, and 1,4-hexadiene.

As used herein all reference to the Periodic Table of the Elements and groups thereof shall be to the version of the Table published by the Handbook of Chemistry and Physics, CRC Press, 1987, utilizing the IUPAC system for naming groups.

Preferred metal coordination complexes are Group 4 or Lanthanide based complexes. Further preferred complexes are those comprising a delocalized $\theta^5$ bonded group which is a cyclopentadienyl or substituted cyclopentadienyl group which forms a ring structure with the metal atom. Preferred delocalized n-bonded moieties are cyclopentadienyl-, indenyl-, and fluorenyl groups, and saturated derivatives thereof which form a ring structure with the metal atom. Each carbon atom in the cyclopentadienyl radical may be substituted or unsubstituted with the same or a different radical selected from the group consisting of hydrocarbyl radicals, substituted-hydrocarbyl radicals wherein one or more hydrogen atoms are replaced by halogen atoms, and hydrocarbyl-substituted metalloid radicals wherein the metalloid is selected from Group 14 of the Periodic Table of the Elements. In addition two or more such substituents may together form a fused ring system. Suitable hydrocarbyl and substituted-hydrocarbyl radicals, which may be substituted for at least one hydrogen atom in the cyclopentadienyl radical, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Suitable organometalloid radicals include mono-, di- and trisubstituted organometalloid radicals of Group 14 elements wherein each of the hydrocarbyl groups contain from 1 to about 20 carbon atoms. More particularly, suitable organometalloid radicals include trimethylsilyl, triethylsilyl, ethyldimethylsilyl, methyldiethylsilyl, phenyldimethylsilyl, methyldiphenylsilyl, triphenylsilyl, triphenylgermyl, trimethylgermyl and the like.

In the previously disclosed Formula I, suitable anionic ligand groups, X, are illustratively selected from the group consisting of hydride, halo, alkyl, silyl, germyl, aryl, amide, aryloxy, alkoxy, phosphide, sulfide, aceyl, pseudo halides such as cyanide, azide, etc., acetylacetonate, etc., or a combination thereof.

A highly preferred metal coordination complex corresponds to the formula:

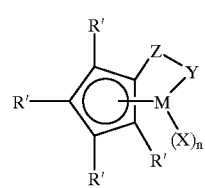

III wherein R' each occurrence is independently selected from the group consisting of hydrogen, alkyl, aryl, silyl, germyl, cyano, halo and combinations thereof having up to 20 non-hydrogen atoms;

X each occurrence independently is selected from the group consisting of hydride, halo, alkyl, aryl, silyl, germyl, aryloxy, alkoxy, amide, siloxy, and combinations thereof having up to 20 non-hydrogen atoms, provided that in at least one occurrence X is halogen;

Y is —O—, —S—, —NR*—, or —PR*—;

M is a is a Group 4 metal in the +4 oxidation state;

n is 2; and

Z is SiR*$_2$, CR*$_2$, SiR*$_2$SiR*$_2$, CR*$_2$CR*$_2$, CR*=CR*, CR*$_2$SiR*$_2$, GeR*$_2$, or BR*; wherein:

R* each occurrence is independently selected from the group consisting of hydrogen, alkyl, aryl, silyl, halogenated alkyl, halogenated aryl groups having up to 20 non-hydrogen atoms, and mixtures thereof, or two or more R* groups from Y, Z, or both Y and Z form a fused ring system.

It should be noted that the complex may exist as a dimer or higher oligomer and that neutral Lewis base ligands such as ether, phosphine and amine compounds may be also associated with the complexes.

Further preferably, Y is a nitrogen or phosphorus containing group corresponding to the formula —N(R"")— or —P(R"")—, wherein R"" is $C_{1-10}$ alkyl or aryl, ie. an amido or phosphido group.

Most highly preferred complex compounds prepared according to the present invention are amidosilane- or amidoalkanediyl- compounds corresponding to the formula:

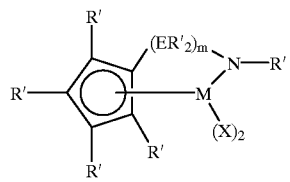

IV wherein:

M is titanium, zirconium or hafnium in the +4 oxidation state, bound in an $\eta^5$ bonding mode to the cyclopentadienyl group;

R' each occurrence is independently selected from the group consisting of hydrogen, silyl, alkyl, aryl and combinations thereof having up to 10 carbon or silicon atoms;

E is silicon or carbon;

X independently each occurrence is hydride, halo, alkyl, aryl, aryloxy or alkoxy of up to 10 carbons, provided that in at least one occurrence X is halogen; and m is 1 or 2.

Most preferred complexes are titanium or zirconium complexes.

Examples of the most highly preferred metal coordination complexes formed according to the present invention include compounds wherein the R' on the amido group is methyl, ethyl, propyl, butyl, pentyl, hexyl, (including isomers), norbornyl, benzyl, phenyl, etc.; the cyclopentadienyl group is cyclopentadienyl, indenyl, tetrahydroindenyl, fluorenyl, octahydrofluorenyl, etc.; R' on the foregoing cyclopentadienyl groups each occurrence is hydrogen, methyl, ethyl, propyl, butyl, pentyl, hexyl, (including isomers), norbornyl, benzyl, phenyl, etc.; and X is chloro, bromo, iodo, methyl, ethyl, propyl, butyl, pentyl, hexyl, (including isomers), norbornyl, benzyl, phenyl, etc. Specific compounds include: (tert-butylamido)(tetramethyl-$\eta^5$-cyclopentadienyl)-1,2-ethanediylzirconium dichloride, (tert-butylamido)(tetramethyl-$\eta^5$-cyclopentadienyl)-1,2-ethanediyltitanium dichloride, (methylamido) (tetramethyl-$\eta^5$-cyclopentadienyl)-1,2-ethanediylzirconium dichloride, (methylamido)(tetramethyl-$\eta^5$-cyclopentadienyl)-1,2-ethanediyltitanium dichloride, (ethylamido)(tetramethyl-$\eta^5$-cyclopentadienyl)-methylenetitanium dichloride, (tert-butylamido)dibenzyl(tetramethyl-$\eta^5$-cyclopentadienyl)-silanezirconium benzyl chloride, (benzylamido)dimethyl-(tetramethyl-$\eta^5$-cyclopentadienyl)silanetitanium dichloride, (phenylphosphido)dimethyl(tetramethyl-$\eta^5$-cyclopentadienyl)silanezirconium benzyl chloride, and the like.

The complexes are prepared by contacting the metal reactant and a Group I metal derivative or Grignard derivative of the cyclopentadienyl compound in a solvent and separating the salt byproduct. Suitable solvents for use in preparing the metal complexes are aliphatic or aromatic liquids such as cyclohexane, methylcyclohexane, pentane, hexane, heptane, tetrahydrofuran, diethyl ether, benzene, toluene, xylene, ethylbenzene, etc., or mixtures thereof.

An organic halide is then employed to raise the oxidation state of the metal in the complex. The oxidation is accomplished merely by contacting the complex and the organic halide, optionally in the presence of a solvent. Preferred are the use of inert solvents, particularly tetrahydrofuran, and temperatures from 0 to 100° C., more preferably 25 to 60° C. The reaction is unique in that a one electron oxidation occurs. Only the halogen is incorporated into the metal complex and the organic remnant is believed to become a neutral organic molecule.

Numerous organic halides may be used for the oxidation according to the present invention. Examples include methyl chloride, methylene chloride, chloroform, carbon tetrachloride, 1,1,1-trichloroethane, tetrachloroethylene, 1-chloropropane, 1-chlorodecane, benzylchloride, chlorobenzene, a solution of polyvinylchloride dissolved in a suitable solvent, etc. The corresponding bromine or iodine containing organic halides may also be used if desired. Preferred organic halides are $C_{1-12}$ alkylchlorides having from 1 to 10 chlorine atoms. Particularly preferred organic halides are methylehloride, methylene chloride, chloroform, and carbon tetrachloride.

The quantity of organic halide employed in the oxidation is suitably at least one equivalent based on halogen content for each mole of metal compound to be oxidized. Large excesses of organic halide can also be used without detriment. Preferred ratios of organic halide (equivalents based on halogen content: moles metal compound) are from 1:1 to 10,000:1, preferably 1:1 to 100:1, most preferably 1:1 to 1.5:1.

In order to assist in the handling of the metal compounds employed in the present process corresponding to the formula $MX_{n+1}$, it may be beneficial first to form a solid adduct thereof by the use of a suitable coordinating agent according to well known techniques in the art. For example, whereas titanium tetrachloride is a fuming liquid which is difficult to handle, one may first form an adduct of $TiCl_3$ with an ether, tertiary amine, tertiary phosphine or other basic nonprotic compound. The resulting solids may be more easily handled. A preferred coordinating adduct is tetrahydrofuran.

The reactions employed in preparing the metal complex may be conducted either heterogeneously or homogeneously. That is, the various reactants or the resulting product need not be substantially soluble in the solvent mixture. Generally the reactants are contacted under an inert atmosphere for a time from several minutes to several days. Agitation may be employed if desired. The temperature of the reaction is generally from –90° C. to 150° C., preferably from –20° C. to 70° C.

Suitable catalysts for use according to the present invention are prepared by combining the metal coordination compound and activating cocatalyst compound in any order and in any suitable manner. Preferably the ratio of the coordination complex and cocatalyst on a molar basis is from about 1:0.1 to about 1:10,000. It will, of course, be appreciated that the catalyst system may also be formed in situ if the components thereof are added directly to the polymerization process and a suitable solvent or diluent, including condensed monomer, is used in said polymerization process. Suitable solvents include toluene, ethylbenzene, alkanes and mixtures thereof. In certain cases the catalysts may be isolated from solution and retained under inert atmosphere prior to use. The catalysts' components are sensitive to both moisture and oxygen and should be handled and transferred in an inert atmosphere such as nitrogen, argon or helium or under vacuum.

Polymerizations using the catalyst of the present process are conducted according to known techniques for Ziegler-Natta or Kaminsky-Sinn type polymerizations. That is, the monomer(s) and catalyst are contacted at a temperature from −30° C. to 250° C., at reduced, elevated or atmospheric pressures. The polymerization is conducted under an inert atmosphere which may be a blanketing gas such as nitrogen, argon, hydrogen, ethylene, etc. or under vacuum. Hydrogen may additionally be utilized in the control of molecular weight through chain termination as is previously known in the art. The catalyst may be used as is or supported on a suitable support such as alumina, $MgCl_2$ or silica to provide a heterogeneous supported catalyst. A solvent may be employed if desired. Suitable solvents include toluene, ethylbenzene, and excess vinylidene aromatic or olefin monomer. The reaction may also be conducted under solution or slurry conditions, in a suspension utilizing a perfluorinated hydrocarbon or similar liquid, in the gas phase, ie. utilizing a fluidized bed reactor, or in a solid phase powder polymerization. A catalytically effective amount of the present catalyst and cocatalyst are any amounts that successfully result in formation of polymer. Such amounts may be readily determined by the routine experimentation by the skilled artisan. Preferred amounts of catalyst and cocatalyst are sufficient to provide an equivalent ratio of addition polymerizable monomer:catalyst of from $1 \times 10^{10}$:1 to 100:1, preferably from $1 \times 10^8$:1 to 500:1, most preferably $1 \times 10^6$:1 to 1000:1. The cocatalyst is generally utilized in an amount to provide an equivalent ratio of cocatalyst:catalyst from 10,000:1 to 0.1:1, preferably from 1,000:1 to 1:1.

It is to be understood that the metal complex may undergo various transformations or form intermediate species prior to and during the course of a polymerization. Thus other precursors could possibly be conceived to achieve the same catalytic species as are herein envisioned without departing from the scope of the present invention.

The resulting polymeric product is recovered by filtering or other suitable technique. Additives and adjuvants may be incorporated in the polymers of the present invention in order to provide desirable characteristics. Suitable additives include pigments, UV stabilizers, antioxidants, blowing agents, lubricants, plasticizers, photosensitizers, and mixtures thereof.

Preferably such polymers possess a Mw of greater than 13,000, more preferably greater than 20,000 and most preferably greater than 30,000. Also preferably such polymers possess a melt index ($I_2$), ASTM D-1238 Procedure A, condition E, of less than 125, more preferably from 0.01–100 and most preferably from 0.1 to 10.

Prior to polymerization according to the present process the monomers and solvents, if any, may be purified by vacuum distillation, and/or contacted with molecular sieves, silica, or alumina to remove impurities. In addition, reactive blanking agents, such as trialkylaluminum compounds, alkali metals and metal alloys, especially Na/K, may be used to remove impurities. Preferred operating conditions for such polymerization reactions are pressures from atmospheric to 1000 atmospheres and temperatures from 30° C. to 200° C. Polymerizations at temperatures above the autopolymerization temperature of the respective monomers may contain small amounts of homopolymer polymerization products resulting from free radical polymerization.

Having described the invention the following examples are provided as further illustrative and are not to be construed as limiting. Unless stated to the contrary parts and percentages are based on weight.

Example 1

Preparation of (Tert-butylamido)dimethyl (tetramethyl-$\eta^5$-cyclopentadienyl)silanetitanium dichloride In a drybox, 4.0 mL of 2.0 M isopropylmagnesium chloride in diethyl ether was syringed into a 100 mL flask. The ether was removed under reduced pressure to leave a colorless oil. 20 mL of a 4:1 (by volume) toluene:tetrahydrofuran (THF) mixture was added followed by 0.97 g of (tert-butylamino)dimethyl(tetramethylcyclopentadienyl) silane. The solution was heated to reflux. After 8–10 hours, a white precipitate began to form. After refluxing for a total of 27 hours, the solution was cooled and the volatile materials were removed under reduced pressure. The white solid residue was slurried in pentane and filtered to leave a white powder (1.23 g, 62% yield) of $Me_4C_5SiMe_2N$-t-$BuMg_2Cl_2(THF)_2$.

In the drybox, 0.10 g of $TiCl_3(THF)_3$ was suspended in 40 mL of THF. 0.138 g of solid $Me_4C_5SiMe_2N$-t-$BuMg_2Cl_2$ $(THF)_2$ was added, resulting in a color change from pale blue to deep purple, signifying the formation of the complex (tert-butylamido)dimethyl(tetramethyl-$\eta^5$-cyclopentadienyl)silanetitanium chloride. After stirring for 5 minutes, 0.17 ml of a 1.56 M solution of methylenechloride in tetrahydrofuran was added. The color changed to bright yellow. After several minutes the THF was removed under reduced pressure. The product was recovered by extraction in pentane. The yield was 70 percent. The product's identity was confirmed as (tert-butylamido)dimethyl(tetramethyl-$\eta^5$-cyclopentadienyl)silanetitanium dichloride by $^1$H NMR, ($C_6D_6$): δ1.992 (s), 1.986 (s), 1.414 (s), 0.414 (s).

Polymerization of Styrene/ Ethylene

Polymerization of a styrene/ethylene mixture was accomplished by combining 1.65 mL of a 10% solution of MAO in toluene with a solution of 45 mL of toluene and 50 mL styrene in a stainless steel shot tank. 250 μL of a 0.010 M solution of (tert-butylamido)dimethyl-(tetramethyl-$\eta^5$-cyclopentadienyl)silanetitanium dichloride was added to 2.5 mL of toluene in a second shot tank. Both shot tanks were sealed, removed from the glove box, and attached to a 600 mL stainless steel pressure vessel. The pressure vessel was evacuated and purged with argon.

The styrene/toluene/MAO solution was added to the pressure vessel and warmed to 89° C. under 620 kPa (90 psig) ethylene with stirring. At this time the catalyst solution was added and the pressure was increased to 1275 kPa (185 psig) and regulated between 1240–1275 Kpa (180–185 psig). An exotherm raised the temperature to 95° C. The temperature was lowered to 90° C. and was then regulated between 90–92° C. for the remainder of the reaction.

After 1.0 hr. the ethylene feed was discontinued. The reaction was vented to the atmosphere and cooled to 30° C.

at which time methanol was added. The product was collected, washed with methanol and residual solvents were removed under reduced pressure at 120° C. which resulted in 9.02 g of material. $^{13}$C NMR analysis of this material showed it to be a random copolymer of styrene (15.2% on a molar basis) and ethylene, free of peaks attributed to polystyrene.

(Olefin Polymerization)

Ethylene was polymerized by combining 5 mL of a 1 M solution of triethyl aluminum in mixed $C_6$ alkane solvent and 0.5 mL of a 0.01 M solution of (tert-butylamido)dimethyl(tetramethyl-$\eta^5$-cyclopentadienyl)silanetitanium dichloride in toluene in a stainless steel (SS) shot tank. The titanium catalyst and triethyl aluminum cocatalyst solution was then added under pressure to a 3 L SS pressure vessel containing 2 L of mixed alkane solvent (Isopar™ E, available from Exxon Chemicals, Inc.) under 3100 kPa (450 psig) ethylene at 150° C. The reaction temperature was maintained at 150° C. for 10 minutes. The ethylene pressure was held constant, and a mass-flow meter measured the uptake of ethylene to be 15.7 g. The polymer solution was then removed from the pressure vessel and the polyethylene was recovered after drying under reduced pressure at 90° C. overnight. Yield was 15.7 g.

Example 2

In a drybox, 0.20 g of $TiCl_3(THF)_3$ was suspended in 40 mL of THF. 0.277 g of solid $Me_4C_5SiMe_2N$-t-$BuMg_2Cl_2$ $(THF)_2$ was added, resulting in a color change from pale blue to deep purple. After stirring for 5 minutes, 0.17 ml of a 1.56 M solution of methylene-chloride in tetrahydrofuran was added. The color changed to bright yellow over a period of one hour. The THF was removed under reduced pressure. The product was recovered by extraction in pentane. The yield of the bright yellow (tertbutylamido)dimethyl(tetramethyl-n5-cyclopentadienyl)silanetitanium dichloride was 0.144 g 72.4 percent.

Example 3

In a drybox, 0.384 g of $TiCl_3(THF)_3$ was suspended in 40 mL of THF. 0.513 g of solid $Me_4C_5SiMe_2N$-t-$BuMg_2Cl_2$ $(THF)_2$ was added, resulting in a color change from pale blue to deep purple. After stirring for 5 minutes, 0.1 ml of carbon tetrachloride was added. The color changed immediately to bright yellow. After stirring for ten minutes the THF was removed under reduced pressure. The product was recovered by extraction in pentane. The yield of the bright yellow (tertbutylamido)dimethyl(tetramethyl-n5-cyclopentadienyl)silanetitanium dichloride was 0.266 g 69.6 percent.

I claim:

1. A process for preparing a metal coordination complex corresponding to the formula:

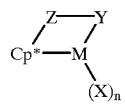

wherein:

M is a metal of Group 4, or the Lanthanide series of the Periodic Table of the Elements;

Cp* is a substituted cyclopentadienyl group π-bound in an $\eta^5$ bonding mode to M;

Z is a moiety comprising boron, or a member of Group 14 of the Periodic Table of the Elements, and optionally sulfur or oxygen, said moiety having up to 20 non-hydrogen atoms, and optionally Cp* and Z together form a fused ring system;

X independently each occurrence is an anionic ligand group having up to 30 non-hydrogen atoms, provided that in at least one occurrence X is halide;

n is 1 or 2 depending on the valence of M; and

Y is an anionic ligand group bonded to Z and M comprising nitrogen, phosphorus, oxygen or sulfur and having up to 20 non-hydrogen atoms, optionally Y and Z together form a fused ring system;

the steps of the process comprising:

(A) contacting a metal compound of the formula $MX'_{n+1}$, or a coordinated adduct thereof with a dianionic salt compound corresponding to the formula:

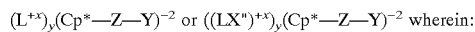

X' independently each occurrence is an anionic ligand group having up to 30 non-hydrogen atoms, L is a metal of Group 1 or 2 of the Periodic Table of the Elements, X" is bromo, chloro or iodo, x and y are either 1 or 2 and the product of x and y equals 2, and X, Cp*, Z, and Y are as previously defined; in an inert solvent to form a complex corresponding to the formula:

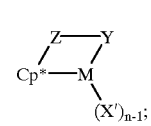

(B) contacting the resulting complex with an organic halide under reaction conditions suitable to raise the oxidation state of the metal and incorporate only the halogen ligand from the organic halide into the complex; and (C) recovering the resulting product;

wherein the process is characterized by the fact that only the halogen ligand from the organic halide is incorporated into the complex.

2. A process according to claim 1 wherein the metal, M, is titanium or zirconium.

3. A process according to claim 1 wherein the organic halide is a $C_{1-12}$ alkylchloride having from 1 to 10 chlorine atoms.

4. A process according to claim 3 wherein the organic halide is methylchloride, methylene chloride, chloroform or carbon tetrachloride.

5. The process of claim 1 wherein the organic halide is methyl chloride, methylene chloride or chloroform.

* * * * *